US007885378B2

(12) United States Patent
Kopans et al.

(10) Patent No.: US 7,885,378 B2
(45) Date of Patent: Feb. 8, 2011

(54) IMAGING SYSTEM AND RELATED TECHNIQUES

(75) Inventors: Daniel B. Kopans, Waban, MA (US); Richard H. Moore, Concord, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 12/090,314

(22) PCT Filed: Oct. 4, 2006

(86) PCT No.: PCT/US2006/038828

§ 371 (c)(1),
(2), (4) Date: Apr. 15, 2008

(87) PCT Pub. No.: WO2007/047114

PCT Pub. Date: Apr. 26, 2007

(65) Prior Publication Data

US 2008/0285712 A1 Nov. 20, 2008

Related U.S. Application Data (60) Provisional application No. 60/728,546, filed on Oct. 19, 2005.

(51) Int. Cl.
*A61B 6/00* (2006.01)
*G01N 23/00* (2006.01)

(52) U.S. Cl. .............................. 378/21; 378/9; 378/13; 378/26; 378/37

(58) Field of Classification Search .................. 378/13, 378/21, 22, 24–27, 9, 37
See application file for complete search history.

(56) References Cited

U.S. PATENT DOCUMENTS

| 3,746,872 | A | 7/1973 | Ashe et al. |
| 4,134,020 | A | 1/1979 | Zonneveld |
| 4,200,799 | A | 4/1980 | Saito |
| 4,442,534 | A | 4/1984 | Haendle et al. |
| 4,464,777 | A | 8/1984 | Machida |
| 4,922,512 | A | 5/1990 | Lajus et al. |
| 5,060,246 | A | 10/1991 | Van Der Brug et al. |
| 5,359,637 | A | 10/1994 | Webber |
| 5,511,106 | A | 4/1996 | Doebert et al. |
| 5,872,828 | A | 2/1999 | Niklason et al. |
| 6,005,908 | A | 12/1999 | Oppelt et al. |

(Continued)

FOREIGN PATENT DOCUMENTS

EP 0 224 886 6/1987

(Continued)

OTHER PUBLICATIONS

PCT International Preliminary Report on Patentability from WIPO for PCT/US2006/038828 dated May 2, 2008.

(Continued)

*Primary Examiner*—Hoon Song
*Assistant Examiner*—Mona M Sanei
(74) *Attorney, Agent, or Firm*—Quarles & Brady LLP (57) ABSTRACT

An imaging method and apparatus is described in which distances between a source and an object are changed and projection images are generated at each of the different distances.

18 Claims, 6 Drawing Sheets

U.S. PATENT DOCUMENTS

| | | | |
|---|---|---|---|
| 6,164,820 A | 12/2000 | Hell et al. | |
| 6,233,303 B1 | 5/2001 | Tam | |
| 6,236,708 B1 * | 5/2001 | Lin et al. | 378/22 |
| 6,242,743 B1 | 6/2001 | DeVito et al. | |
| 6,285,733 B1 | 9/2001 | Proksa et al. | |
| 6,289,235 B1 | 9/2001 | Webber et al. | |
| 6,292,531 B1 | 9/2001 | Hsieh | |
| 6,341,156 B1 | 1/2002 | Baetz et al. | |
| 6,375,352 B1 | 4/2002 | Hewes et al. | |
| 6,480,565 B1 | 11/2002 | Ning | |
| 6,545,280 B2 | 4/2003 | Weinberg | |
| 6,574,499 B1 | 6/2003 | Dines et al. | |
| 6,600,803 B2 | 7/2003 | Bruder et al. | |
| 6,611,575 B1 | 8/2003 | Alyssin et al. | |
| 6,618,466 B1 | 9/2003 | Ning | |
| 6,765,981 B2 | 7/2004 | Heumann | |
| 6,765,985 B2 | 7/2004 | Marie et al. | |
| 6,798,790 B1 * | 9/2004 | Enssle et al. | 370/503 |
| 6,970,531 B2 | 11/2005 | Eberhard et al. | |
| 2002/0045833 A1 | 4/2002 | Wake et al. | |
| 2002/0104163 A1 | 8/2002 | Reimann | |
| 2002/0181649 A1 | 12/2002 | Rasche et al. | |
| 2003/0006387 A1 | 1/2003 | Marie et al. | |
| 2003/0043962 A1 | 3/2003 | Lai | |
| 2003/0156678 A1 * | 8/2003 | Hamada et al. | 378/4 |
| 2003/0194050 A1 | 10/2003 | Eberhard et al. | |
| 2003/0194051 A1 | 10/2003 | Wang et al. | |
| 2004/0066882 A1 | 4/2004 | Eberhard et al. | |
| 2004/0131145 A1 | 7/2004 | Ohara | |
| 2005/0089134 A1 | 4/2005 | Bruder et al. | |
| 2005/0113681 A1 | 5/2005 | DeFreitas et al. | |
| 2005/0129172 A1 | 6/2005 | Mertelmeier | |
| 2005/0157841 A1 * | 7/2005 | Chopra | 378/22 |

FOREIGN PATENT DOCUMENTS

| | | |
|---|---|---|
| EP | 0 368 067 | 5/1990 |
| EP | 0 948 930 A1 | 10/1999 |
| GB | 1 316 773 | 5/1973 |
| WO | WO 00/57788 A1 | 10/2000 |
| WO | WO 01/62036 A2 | 8/2001 |
| WO | WO 01/62036 A3 | 8/2001 |

OTHER PUBLICATIONS

Budinger; "Biological and Biomedical Imaging;" Whitaker Summit White Paper: Biological and Biomedical Imaging; Biomedical Engineering Educational Summit Meeting 2000; 4 pages.

PCT Search Report and Written Opinion of the ISA for PCT/US2006/023466, dated Feb. 2, 2007.

PCT Search Report and Written Opinion of the ISA for PCT/US2006/038828 dated Feb. 9, 2007.

Andrew Smith; Full Field Breast Tomosynthesis; Hologic, Inc.; Oct. 2004; 6 pages.

* cited by examiner

IMAGING SYSTEM AND RELATED TECHNIQUES

CROSS REFERENCE TO RELATED APPLICATIONS

This application is a U.S. National Stage of International Patent Application No. PCT/US2006/038828 filed Oct. 4, 2006, and published in the English language, which application claims the benefit of U.S. Provisional Patent Application No. 60/728,546 filed on Oct. 19, 2005 under 35 U.S.C. §119(e), which applications are hereby incorporated herein by reference in their entirety.

FIELD OF THE INVENTION

This invention relates generally to imaging systems and techniques and more particularly to systems and techniques methods for generating tomographic images.

BACKGROUND OF THE INVENTION

As is known in the art, tomosynthesis is a technique for acquiring and processing a series of projection measurements of an object into three dimensional (3D) slice information. In breast tomosynthesis, for example, the breast is held immobile, while a source (such as an X-ray tube) and/or the detector are moved through a series of positions on an arc to generate a sequence of projection measurements (exposures) at different view-angles. Moving the radiation source through an arc requires motorized translational control of a relatively heavy X-ray tube and gantry assembly to generate the projection images. This is generally cumbersome and tends to induce vibrations in the apparatus being moved. The vibrations reduce the ability of the system to image relatively small features of an object.

SUMMARY OF THE INVENTION

In accordance with the present invention, an imaging system includes a source moveable in a direction toward and away from an object to be imaged so as to change an angle at which a source beam passes through the object. By changing the distance between the source and the object being imaged, the source beam passes through the object at differing angles depending upon the distance of the source from the object. The distance between the source and the object is thus changed to achieve variable magnification projections of the object. The variable magnification is achieved due to variable parallax. The source can be moved to provide a requisite number of views (or projections) required to synthesize tomosynthesis slices. In this manner a plurality of projections can be generated (e.g. at least one projection at each of a plurality of different magnification levels) and the data from the projections can be synthesized into tomosynthesis slices. Thus, with this particular arrangement, a method and apparatus permitting the visualization of object features masked in conventional two-dimensional (2D) projection imaging is provided. The distance between the source and object can be changed by moving either the source or the object. In some embodiments a detector can also be moved in place of, or in conjunction with, movement of the source and/or object.

In accordance with a further aspect of the present invention, an imaging technique includes moving at least one of a source and a detector in a direction toward and away from an object to be imaged. The distance between the source and the object (or the distance between the object and the detector) is changed to achieve variable magnification projections of the object. Thus, due to variable parallax generated by magnification imaging, a requisite number of views (or projections) required to synthesize tomosynthesis slices can be provided. In this manner a plurality of projections can be generated (e.g. at least one projection at each of a plurality of different magnification levels) and the projection data can be synthesized into tomosynthesis slices. Thus, with this particular arrangement, a method and apparatus permitting the necessary visualization of lesion features masked in conventional two-dimensional (2D) projection imaging is provided.

The source may be provided as an X-ray tube in which case the source signal corresponds to an X-ray beam. Other types of sources, may of course also be used including but not limited to a neutron beam source, a microwave source and an optical source.

In accordance with the variable magnification tomography technique of the present invention, a series of projection images at variable magnification levels are acquired and can be used to generate a three-dimensional image. This is in contrast to standard tomography techniques in which projection images of an object are acquired from two or more viewpoints obtained by moving the source and/or object translationally with respect to each other. From these images, the radiologist must infer the three-dimensional (3D) structure of the normal and abnormal tissues of the object.

The variable magnification tomography technique of the present invention, on the other hand, employs motion along an axis which is typically substantially normal to an imaging plane of a detector disposed on an opposite side of the object from the source. Since the source need only move toward and away from the object being imaged, translational movement of the source (with respect to the object being imaged) is not required. Since transitional movement of the source is not required, the amount of vibration induced by source movement is lowered which results in the system being able to image relatively small features of an object.

Also, using source and/or detector and/or object motion which is in the same direction as the direction in which the source signal is emitted can eliminate the need to move the source translationally (e.g. along an arc-shaped path about the object being imaged). Since the relative motion of the source and/or object and/or detector is in a single line or direction, this improves the freedom to position objects or patients in desirable configurations for imaging and for procedures (biopsy, needle-localization, ultrasound, etc.).

In accordance with a further aspect of the present invention, an imaging technique includes operating a source and a detector to generate a first projection image of an object, moving at least one of the source, the object and the detector in a direction which changes the distance between the object and at least one of the source and the detector and operating the source and a detector to generate another projection image of the object corresponding to a magnified or de-magnified image of the object. With this particular arrangement, an imaging technique which provides projection images which can be used to generate three dimensional tomographic images without translating the source, object or detector is provided. By changing the distance between the source and/or detector and the object being imaged, a divergent beam passes through the tissues at differing angles depending on the distance of the x-ray source from the structures in the objects being imaged. These images can then by synthesized into tomographic slices. Thus, a three-dimensional image can be generated without moving the source and/or detector in an arc-shape path about the object and without requiring or using any translation motion of the source, object and/or detector.

In accordance with a further aspect of the present invention, a breast tomography system includes a detector and a source which projects a source signal toward the detector, with the source being movable in a direction which is coincident with an axis along which the source provides the source signal. With this particular arrangement, a variable magnification breast tomography technique is provided. Since the source need only move toward any away from the breast to generate images which can be synthesized into tomography slices, a system having reduced vibrations is provided. Conventional tomosynthesis motion (i.e. moving a source and/or detector through a series of positions along an arc-shaped path) can be combined with the variable magnification breast tomography technique, as desired.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Before describing an imaging system and operations performed to generate images, some introductory concepts and terminology are explained.

It should be appreciated that the systems and techniques described herein can be used in a variety of different applications such as breast imaging, therapeutic applications, photoacoustic applications, skin imaging and other applications.

With the above in mind, it should be appreciated that as used herein, the term "source" refers to any type of source which emits a signal which is received by an appropriate detector. Different types of sources can emit different types of signals and for any particular application, those of ordinary skill in the art will recognize how to select a particular type of source (and a corresponding detector) suitable for the particular application.

It should also be appreciated that, in an effort to promote clarity in the description of the claimed subject matter, specific reference and examples are sometimes made herein to a breast imaging application and techniques which are utilized in breast imaging. Such references should not be taken as limiting the claimed system and techniques to breast imaging applications. Rather, as mentioned above, the present invention finds application in a wide variety of different types of imaging applications including but not limited to therapeutic applications, skin images applications and photoacoustic application.

Figure 1:
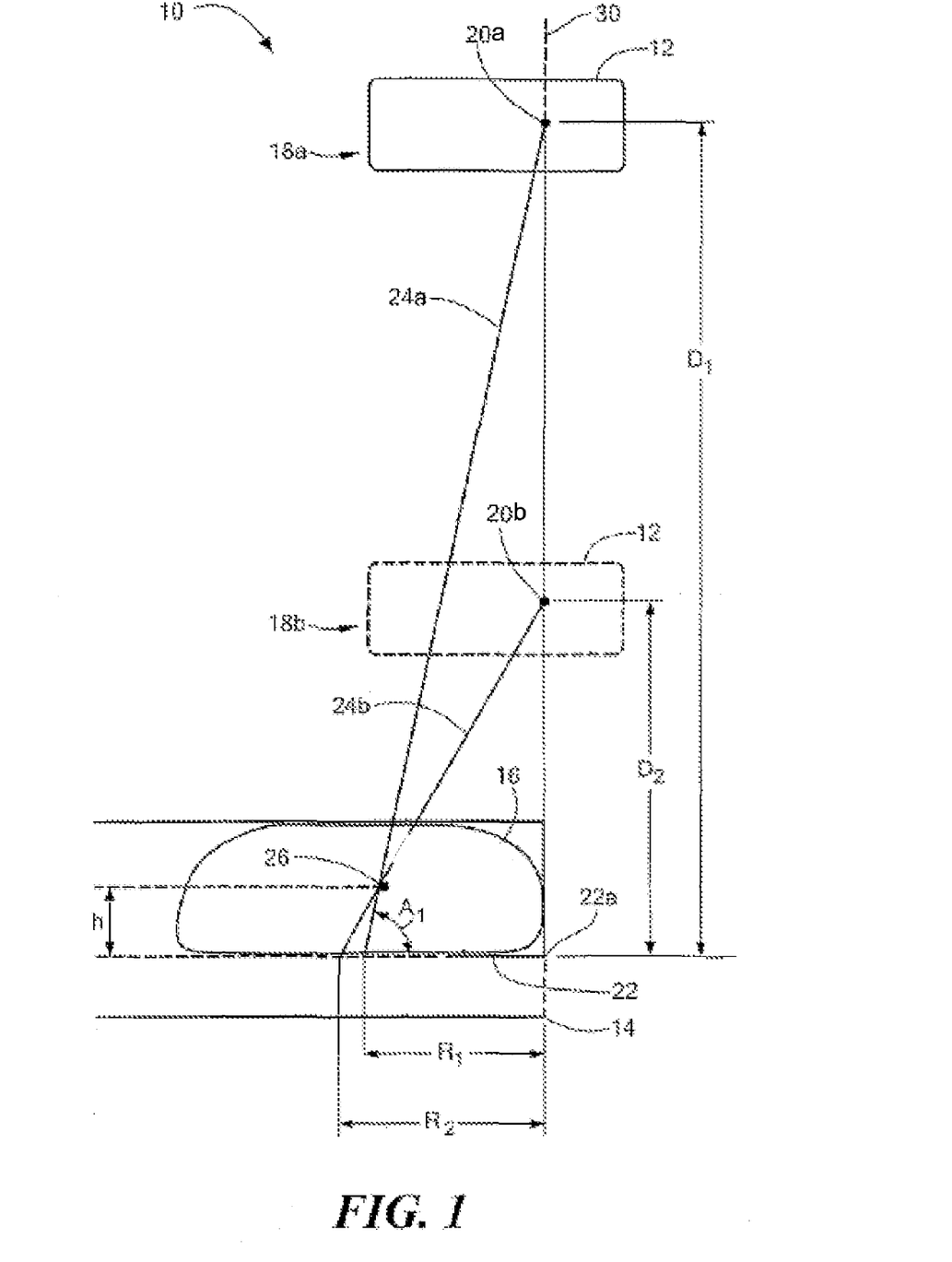
FIG. 1 is a block diagram of an imaging system having variable magnification.

Referring now to FIG. 1, an imaging system 10 includes a source 12 and a detector 14 disposed on opposing sides of an object 16 to be imaged. With the source 12 in a first position 18a, a source focal spot 20a is a first distance above the object 16 and a distance D1 above a detector plane 22. The source 12 emits a divergent beam (or signal) 24a. Thus, with the source 12 in the first position 18a, at least portions of the beam 24a pass through at least portions of the object 16 at a first angle A1 (as measured relative to the plane 22 of the detector 14). In this way, a first projection image of the object 16 can be formed as is generally known.

The source 12 is then moved to a second position 18b such that the source focal spot 20b is a second different distance above the object 16 and a distance D2 above the detector plane 22. The source 12 emits a divergent beam 24b with portions of the beam again intersecting at least a portion of the object 16. It should be appreciated that by changing the distance between the source 12 and the object 16 and in particular of structures or features within the object the angle at which the source beam passes through the object 16 changes. Furthermore, the location at which the beams 24a, 24b impinge upon the detector plane 22 changes. In this manner, different magnification projections of the object 16 and in particular of structures or features within the object can be provided. Thus, by changing the distance between the source and the object, the angle at which the source beam impinges upon and passes through the object (assuming no deflection of the beam by structures within the object) and reaches the detector plane changes and an apparent displacement of the object on the detector plane is provided.

In FIG. 1 for example, structure 26 which is internal to object 16 and a height h above detector plane 22, appears to be located on the detector plane at a distance R1 from an edge 22a of the detector plane when the source is positioned at location 18a. When the source is positioned at location 18b, however, structure 26 appears to be located at a distance R2 from edge 22a of the detector plane. The apparent movement of structure 26 on the detector plane 22 is due to the parallax phenomenon. That is, the structure 26 is apparently displaced as when viewed from two different points that are not on a line with the structure 26 due to the parallax effect.

By moving the source 12 closer to and further away from the object 16, a series of projection images can be generated and these projection images can be synthesized into tomosynthesis slices. To thus generate the desired projections, it is necessary to change the angle at which the beam emitted by source 12 intercepts each particle of the object and is collected by the detector 14. In particular, the signal should be collected in such a way that the data can be used to generate tomographic images. By changing the distance between the source and the object (or the distance between the source and the detector) variable magnification projections of the object are provided. That is to say, due to changing parallax, variable magnification projections are acquired. In this way, a requisite number of such projections required to synthesize tomosynthesis slices can be provided. Thus, by appropriately changing the spacing between the source, object and/or detector, a plurality of projections can be generated at different magnification levels (e.g. at least one projection at each of a plurality of different magnification levels) and these projections can be synthesized into tomosynthesis slices. Inherent in the fan-beam X-ray geometry is the relationship of unique diverging lines-of-position. Each particle within the object being studied is traversed by a line-of-position that places it's attenuation characteristic (or other quantity being measured) at a specific point on the detector, along with other particles along that line-of-position. Changing the magnification changes the combination of particles aligning with a specific point on the detector. Altering magnification insures that the set of object particles combining on the line-of-position for magnification A do not then again combine for the same object particle at magnification B (or any other magnifications). In this way the series of magnifications serves to create a series of unique projections, that when correctly combined reinforce the particle on a selected plane in the object.

It may be desirable to alter the size and shape of the electron fluence impinging on the X-ray tube anode (or other illuminating source of energy) electronically or mechanically to modulate the beam quality. Additionally the angular relationship between the cathode, anode and object may be altered to take advantage of the "heel" of the X-ray beam. Further the focal spot size and inclination may be dynamically adjusted to achieve focal spot size, shape and strength that adjusts to the dynamically changing magnification to optimize delivered dose, detector reception, beam energy quality or other factors useful to best sense the object particles for subsequent or contemporaneous reconstruction.

Although in this exemplary embodiment, the source 12 moves from a first distance away from the object to a second distance away from the object, with the first distance being further away from the object 16 than the second distance (i.e. the source is being moved closer toward the target), the reverse can also be done. That is, the source 12 may be moved away from the object 16 rather than toward the object 16. Alternatively, the source movement may be a random or pseudo-random pattern rather than a movement either continuously toward or away from the object. Suffice it to say that the source movement can be in any direction or with any given pattern (either a random or a predetermined pattern) as long as the angle at which the source beam intercepts the object is appropriately changed.

Alternatively, rather than moving the source to change the beam-object intercept angle, the object itself could be moved either toward or away from the object. Alternatively still, both the object and the detector could be moved, or the detector could be moved or both the source and the detector could be moved or the source, detector and object could all be moved. In the cases in which multiple elements are moved (i.e. multiple ones of source, detector and object), the movement can occur at the same time (and with all elements moving at the same rate of speed or at different rates of speed) or at different times (with the elements moving at the same rate of speed or at different rates of speed).

Alternatively still, it may be possible to alter the angle at which the source beam intercepts the object by changing or otherwise adjusting a characteristic of the beam by altering, modifying or adjusting the source itself. For example, by internally adjusting a characteristic of the source, the beam-width of the beam emitted from the source can be changed which in turn changes the angle at which the beam intercepts an object. As another example, when the source is provided as an X-ray source, the spot size of the x-ray beam within the source can be changed to thus change the angle at which a beam emitted from the source intercepts the object.

The source may be provided as a neutron beam source, a microwave source, an x-ray source or an optical source. One of ordinary skill it the art will understand how to select a particular type of source for a particular application. In breast imaging applications, for example, the source 12 may be provided as an x-ray source which emits a beam having a divergent shape. The beam may be provided having a cone-shape, a fan-shape or any other type of shape having at least a portion which is divergent.

In the system of FIG. 1, the source 12 and/or detector 14 are moveable along an axis 30. In this way, either or both of source 12 and detector 14 can be moved toward or away from the object 16 being imaged.

It should be appreciated that structures that are closer to the imaging detector are magnified less than structures that are further away from the detector when imaged using a divergent incident beam (X-ray, etc.). By obtaining images with the focal spot a multiplicity of different distances from the targeted tissues (including on opposite sides of the targeted tissue), the differences in magnification of the internal structures within an object encodes the depth of those structures This encoded position data can be used to recover the depth data through reconstruction methods that compute the volumetric distribution of attenuation coefficient indices. This can be presented for review as planes or groups of planes for medical review.

One technique which accomplishes this is the superposition of specifically magnified (or de-magnified) projection data such that only the structures in a plane of interest remain in register and reinforce, while structures in other planes do not register and are blurred by misregistration. The so-reinforced structures are more visible by virtue of their brightness and sharpness. The signal to background of the plane of interest relative to the out of plane structures has been raised while that of the out-of-plane structures has been lowered.

It should be appreciated that the magnification factor is a constant. Thus, selection of a particular magnification factor allows selection of the distance above an imaging plane at which the source should be positioned.

The data from the projection images are reconstructed to recover depth information encoded in the apparent movement of tissue structures in the projection images that occurs with varying magnification. This permits the recovery of the depth information and, in the case of breast imaging, the presentation of the breast internal structure as a 3D whole. The 3D whole may be presented as a series of slices or as a 3D rendering for analysis and review.

In one breast imaging embodiment, the number of projection images is in the range of about 7 to about 61. In general, the number of images to use in any particular application is selected to provide the best result (i.e. what the user considers to be the most accurate image). It is desirable to select a number of images which does not result in the individual noise in each image dominating the data. Thus, the particular number of images to select in any application is based upon a number of factors including but not limited to system factors such as source and detector characteristics and the selected image geometry, as well as the number of images which result in substantially maximum reinforcement within the images.

It should also be appreciated that since the strength of the x-ray signal can be reduced as the source moves closer to the object, the overall X-ray dose to which a patient is exposed using the variable imaging technique of the present invention, is comparable to the does to which a patient is exposed using a standard two-view mammography.

Figure 2:
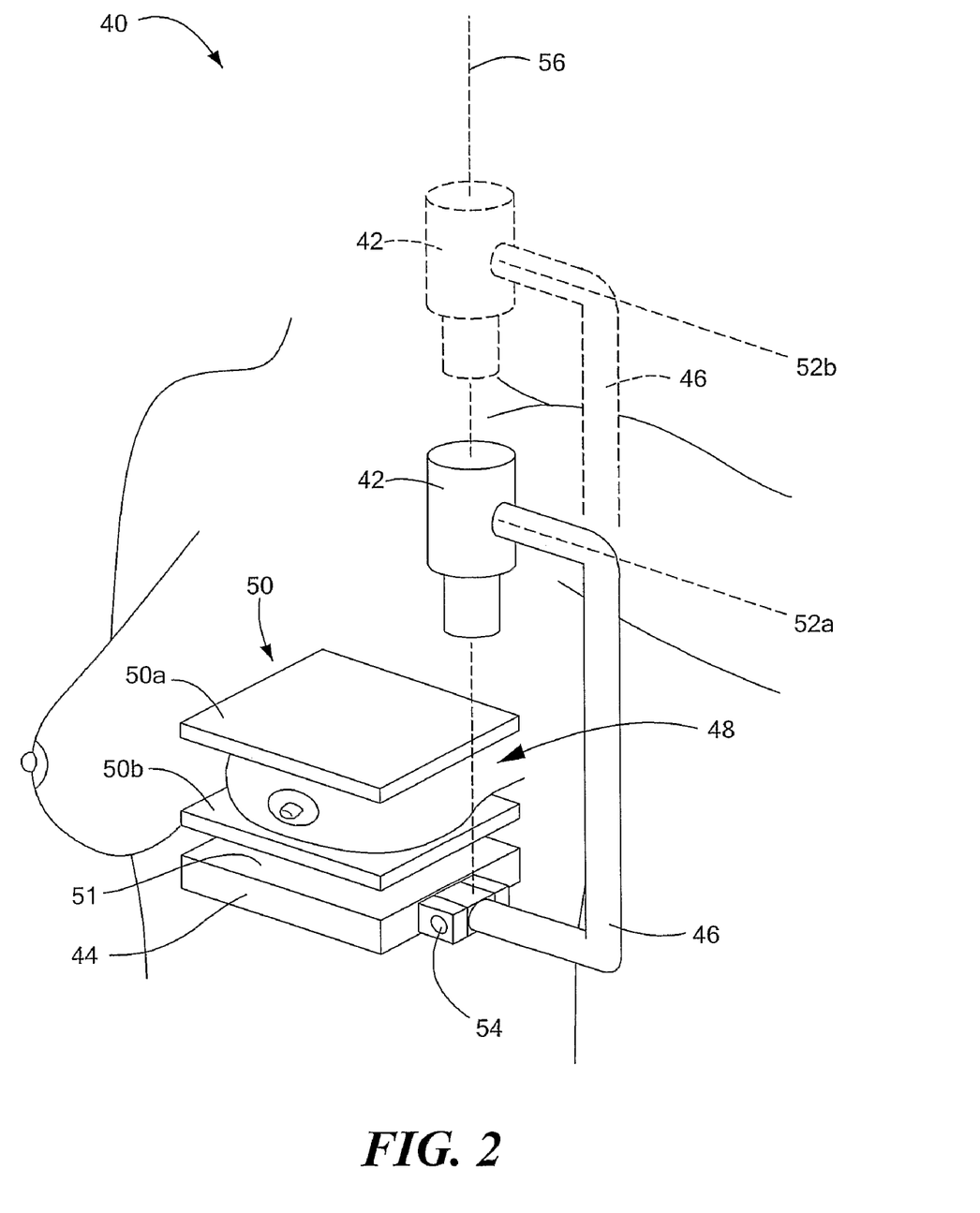
FIG. 2 is an isometric view of a first embodiment of a breast tomography system-having variable magnification.

Referring now to FIG. 2, a breast imaging system 40 includes a source 42 (e.g. an x-ray source) and a detector 44. The detector is here shown as a digital planar detector although other detectors known to those of ordinary skill in the art and having either a flat or curved surface, may of course also be used. It should be appreciated that only the source, detector and a mounting arm 46 are shown in FIG. 2 and that for clarity and ease of description, other parts of the breast imaging system are not shown in FIG. 2.

In the exemplary embodiment of FIG. 2, the source 42 and detector 44 are coupled to first and second opposing ends of a telescoping support arm 46. An object to be imaged (e.g. breast 48) is disposed in a support 50 comprised of compression plates 50a, 50b. Support 50 is decoupled from the source 42, detector 44 and arm 46, such that the support 50, and therefore the breast 48 held in support 50, do not move during movement of the source 42 and/or detector 44 and/or arm 46.

A grid 51 coupled to a top surface of the detector 44 rejects scatter which can occur when the source 42 provides a radiation signal.

The arm 46 and thus the source 50 moves between first and second positions 52a, 52b above the breast 48 and detector 44. In some embodiments, as will be discussed in conjunction with FIGS. 3 and 4, the source 42 and detector 44 may also move about a point 54 located proximate the detector 44.

To generate projection images which can be synthesized into tomosynthesis slices, it is necessary to change the angle at which the beam emitted by source 42 intercepts the breast 48 and is collected by the detector 44. As the arm 46 telescopes up and down (e.g. away from and toward detector 44 between positions 52a, 52b) the source 42 moves up and down along in a direction along an axis 56. As the source moves (e.g. between positions 52a, 52b), the angle at which signals emitted from the source 42 pass through the breast 48 change. Thus, by moving the source closer to and further away from the breast 48, a series of projection images can be generated and these projection images can be synthesized into tomosynthesis slices.

Throughout the movement between positions, the source and detector 44 maintain a known positional relationship. Also, the signal should be collected in such a way that the data can be used to generate tomographic images. By changing the distance between the source and the breast (or the distance between the breast and the image plane of the detector) variable magnification projections of the object are provided. That is to say, due to the variable parallax effect resultant from variable magnification imaging (i.e. changing a distance between a source, an object and/or a detector), the requisite number of views (or projections) required to synthesize tomosynthesis slices can be provided. In this manner (i.e. by appropriately changing the spacing between the source, object and/or detector), a plurality of projections can be generated at different magnification levels (e.g. at least one projection at each of a plurality of different magnification levels) and these projections can be synthesized into tomosynthesis slices.

In operation of the system 40, the radiation source 42 emits a beam of radiation toward the detector 44. The detector detects portions of the radiation after passing through the breast and then the source moves to a different distance above the breast and detector. In some embodiments, the source and detector may also pivot about the point 54. Throughout this motion, the breast 48 and the detector 44 are disposed in the path of the radiation emitted by the source 42 and the source 42 and detector 44 maintain a known spatial relationship.

It should be appreciated that using motion in the same direction as the direction in which the x-ray beam is emitted decreases or in some cases can even eliminate, the size of the swept zone (i.e. the size of the arc over which the source moves) and improve the freedom to position patients in desirable configurations for imaging and for procedures (biopsy, needle-localization, ultrasound, etc.)

It should also be appreciated that source 42 and detector 44 are not aligned with the center of the compression plates. Rather, source 42 and detector 44 are aligned along an edge of the breast and possibly aligned slightly outside of the breast as indicated by axis 56. This is to avoid a "blind spot" appearing in a portion of the breast projections being obtained. In FIG. 1 for example, structure 26 which is internal to object 16 and a height h above detector plane 22, appears to be located on the detector plane at a distance R1 from an edge 22a of the detector plane when the source is positioned at location 18a. When the source is positioned at location 18b, however, structure 26 appears to be located at a distance R2 from edge 22a of the detector plane. The apparent movement of structures within the breast on the detector plane 22 is due to the parallax phenomenon (i.e. view a structure from two different view points). However, the apparent movement does not apply to those structures that are on a line with the two different view points. Thus, the preferred position of the source and detector is that they be offset from the object and structures of interest. Although in FIG. 2 the source is shown offset on one particular side, the source can also be offset on the opposite side as that shown in FIG. 2.

Figure 3:
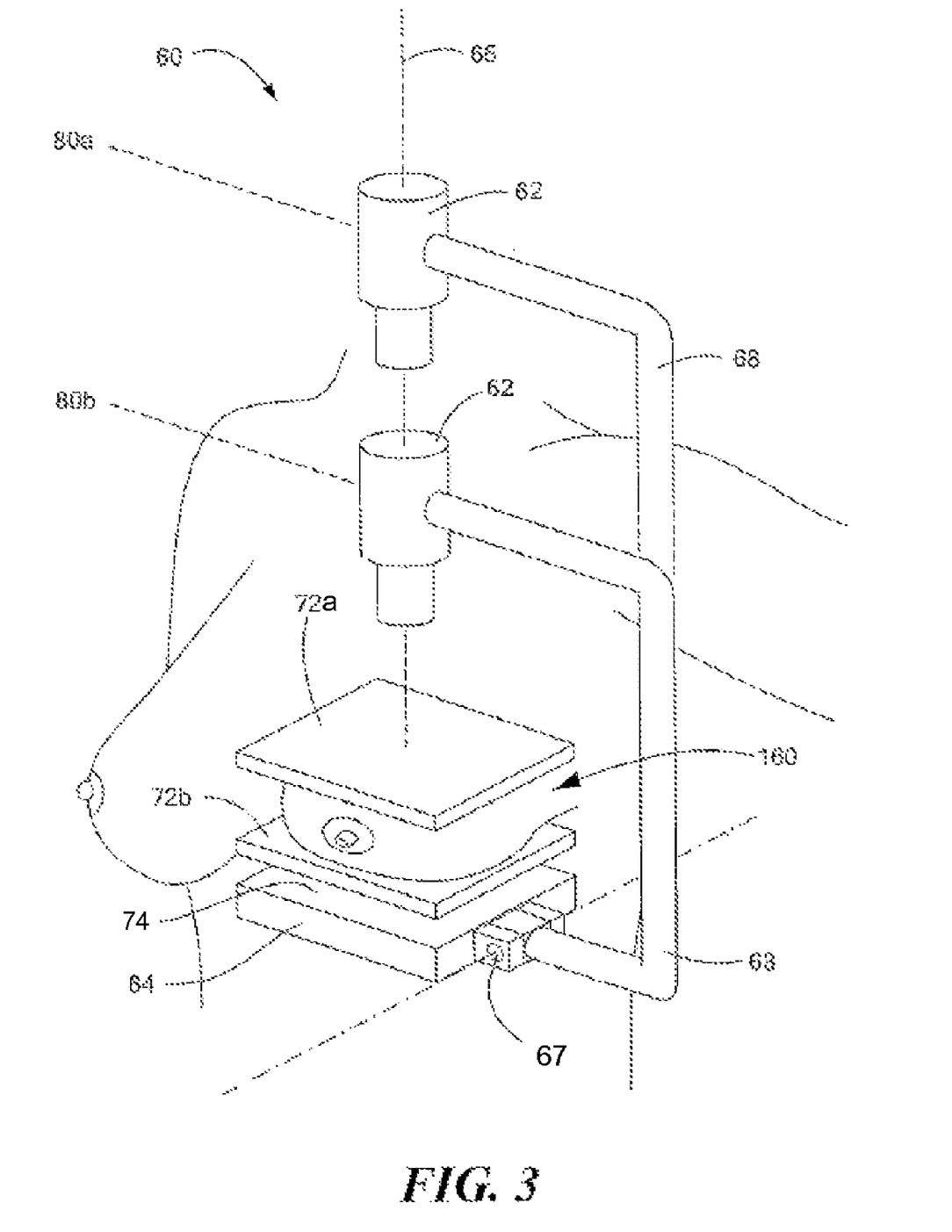
FIG. 3 is an isometric view of a second embodiment of a breast tomography system having variable magnification.
Figure 4:
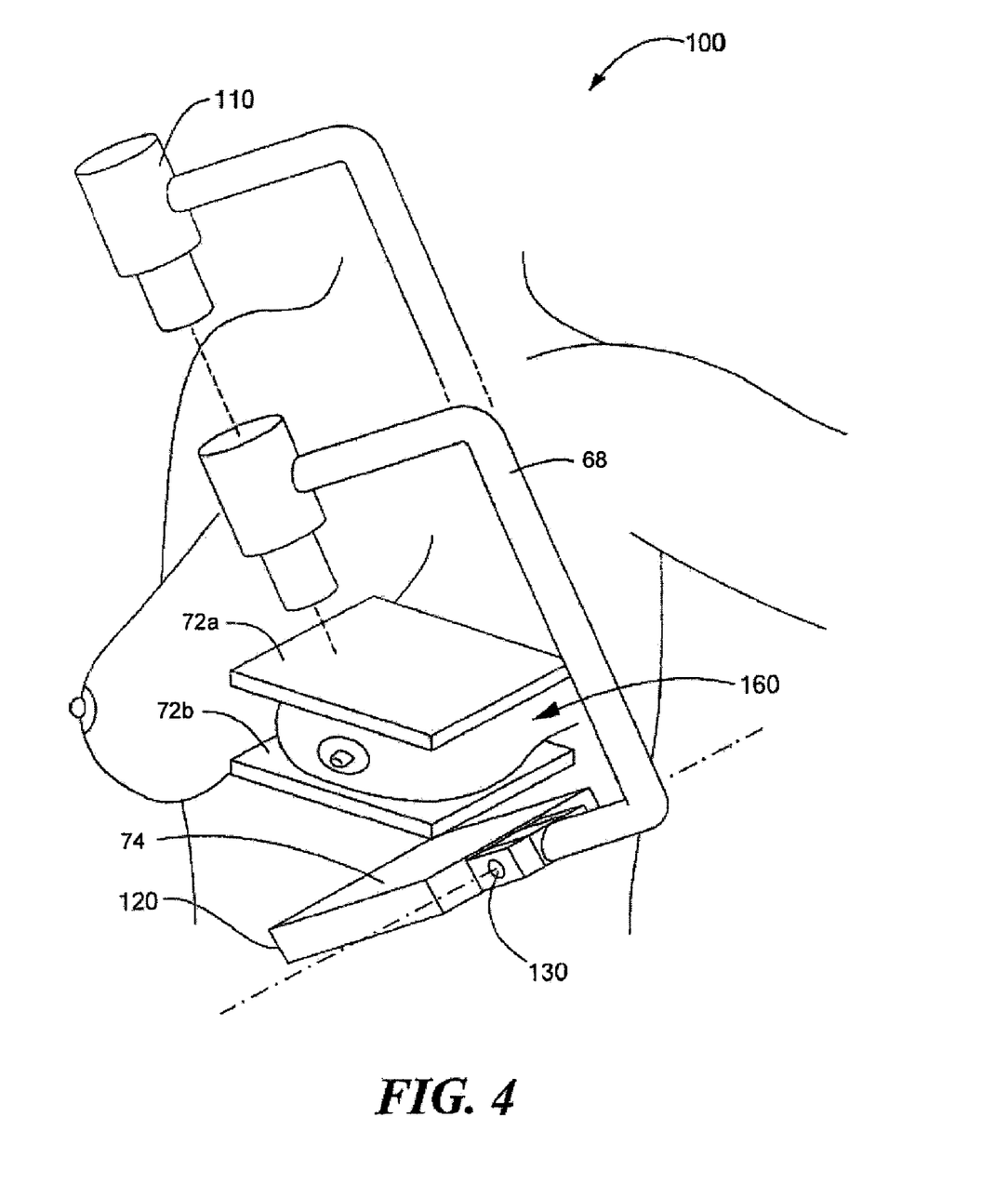
FIG. 4 is an isometric view of a second embodiment of abreast tomography system having variable magnification.

Referring now to FIGS. 3 and 4 in which like elements are provided having like reference designations, a breast tomography system 60 includes a source 62 (e.g. an x-ray source) and a detector 64. Surfaces of the source and detector are spaced from each other by a known distance during operation of the tomography system 60. The detector is here shown as a digital planar detector although other detectors known to those of ordinary skill in the art and having either flat or curved surface, may of course also be used. It should be appreciated that only the source, detector and mounting arms are shown in FIGS. 3 and 4 and that for clarity and ease of description, other parts of the breast tomography system are not shown in FIGS. 3 and 4.

The breast imaging system embodiment of FIGS. 3 and 4 is similar to that shown in FIG. 2 in that the source moves with respect to the object being imaged (i.e. the system allows the variable magnification approached to be used). There are, however, several differences. In the embodiment of FIG. 3, for example, the source is aligned with the approximate center of the breast along an axis 66 (rather than about a periphery of the breast as shown in FIG. 2). Also, in the embodiment of FIGS. 3 and 4, the source and detector are movable about a pivot point 67.

In the exemplary embodiment of FIG. 3, the source 60 and detector 64 are coupled to first and second opposing ends of a telescoping support arm 68. An object to be imaged (e.g. breast 160) is disposed in a support comprised of compression plates 72a, 72b which is decoupled from the source, detector and arm, such that the support (and therefore the breast held in the support) do not move during movement of the source, detector and arm. A grid 74 coupled to a top surface of the detector 120 rejects scatter which can occur when the source 110 provides a radiation signal.

The arm 68 (and thus the source and detector coupled to the arm) moves about a point 67 located proximate the detector. In the exemplary embodiment of FIGS. 3 and 4, point 68 lies in a plane in which the detector lies. As the arm 68 moves, the source 62, detector 64 and arm 68 move through a path (e.g. an arc-shaped path) to the positions shown in FIG. 4. Throughout the movement between positions, the detector 64 maintains a spatial relationship with the source 62 consistent with breast tomography techniques.

In operation of the tomography system 60, the radiation source emits a beam of radiation toward the detector and the source moves between position 80a and position 80b. The source and detector can also pivot about the point 130. Although the spacing between the source and detector can change to provide variable magnification, the breast and the detector are disposed in the path of the radiation emitted by the source and the source and detector and maintain a known spatial relationship in accordance with conventional breast tomography techniques even if the source and detector are moving with a pivot motion as well as along axis 66. The detector 120 detects the presence of any radiation which passes through the breast 160 and reaches the detector 120.

In the case where the system 100 is used to perform breast tomography, a person is positioned as shown in FIGS. 3 and 4 and the breast being imaged (i.e. breast 160 in FIGS. 3 and 4) is placed and compressed between compression plates 72a, 72b. It should be appreciated that the breast may be supported or held in some other manner rather than via the compression plates. Regardless of how the breast is supported or held, the source and detector move to measure data over a range of angles which is wider than possible with prior art breast imaging techniques utilized with a person in the standing position. The data will later be used to provide images of the breast.

Since in accordance with the present invention the source and detector can be moved to positions not possible with prior art systems, the system can provide data which cannot be provided with prior art systems. Thus, the system is able to provide more detailed imaging than prior art systems.

Furthermore, since the source can traverse a range of angles which is wider than the range available in prior art systems, the source can utilize a radiation beam having a cone shape which has a beamwidth and/or beam shape which is narrow compared with the beamwidth and/or beam shape of cone-shaped beams used in prior art systems. This allows use of a radiation beam which lessens the amount of radiation which impinges upon structures that are not of interest. In breast-imaging, for example, it is possible to lessen the amount of radiation which impinges upon a person's chest, shoulder, heart and lungs and it is also possible to lessen the amount of radiation which "spills over" the detector.

Figure 5:
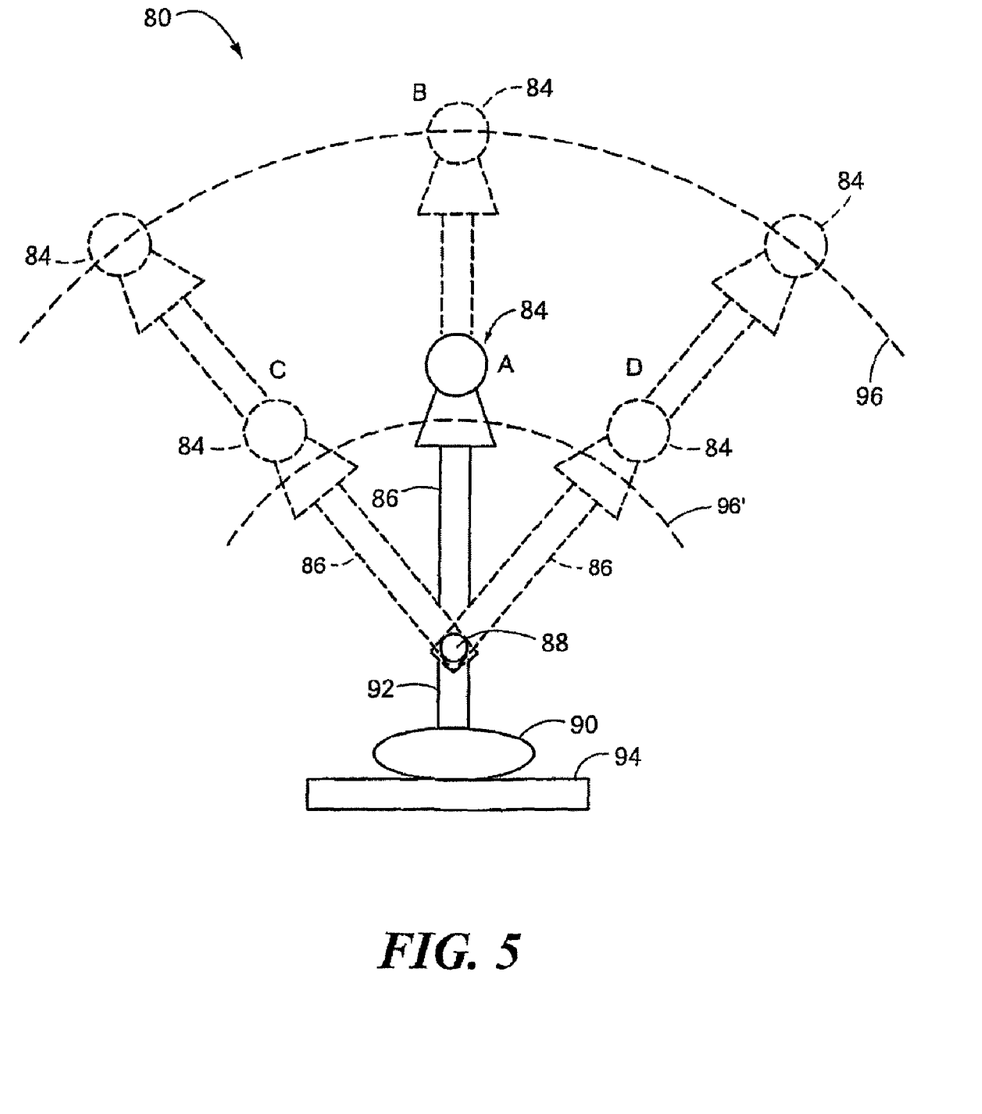
FIG. 5 is a schematic of a tomosynthesis system.

Referring now to FIG. 5, a tomosynthesis system 80 is shown. This system is similar to one described in U.S. Pat. No. 5,872,828 to Niklason et al. and assigned to the assignee of the present application. The system 80 includes a radiation source 84 attached to a movable arm 86 which provides both translational movement and telescoping movement. Thus, movable arm 86 pivots about an axis or pivot point 88, located between the source 82 and an object 90 being imaged (e.g. a breast) and also telescopes (i.e. extends and contracts it's length) which allows the source 84 to move closer to and further away from the object being imaged 90

A fixed arm 92 has a first end attached to a radiation detector 94 and a second end attached to the movable arm 86 at the pivot point 88. The object being imaged 90 (e.g., a human breast) is disposed abutting the detector 94. Typically the object 90 being imaged is compressed against the detector 94.

In use, the source 84 is moved between the source position denoted A and the source position denoted B (referred to as variable magnification motion). The source can also be moved along an arc 96 between positions C and D. Using an arc motion in conjunction with the variable magnification motion can help eliminate artifacts in the image.

The source 84 provides radiation to a detector 94 while moving between the two positions A, B shown in FIG. 5 or while moving between positions C and D along arc 96 or 96'. At any point along the arc, the moveable arm 86 can be extended or contracted by a known amount so as to change the distance (i.e. height) between the source and detector at any given angle. The detector 94 remains stationary. From the information collected by detector 94, a final synthesized representation of the X-ray absorption of the object 90 can be produced as is generally known. The breast imaging system thus utilizes variable magnification to generate tomographic slices by enabling the source to move in directions toward and away from the object and able to translate about the object along an arc shaped path.

It should be appreciated that by allowing the source 84 to move about the object 90 in a straight line or in an arc shaped path (or even is some irregular pattern which includes both translation and variable magnification movement), a source which emits a spot beam (vs. a divergent beam such as a cone-shaped or fan-shaped beam) can be used.

Figure 6:
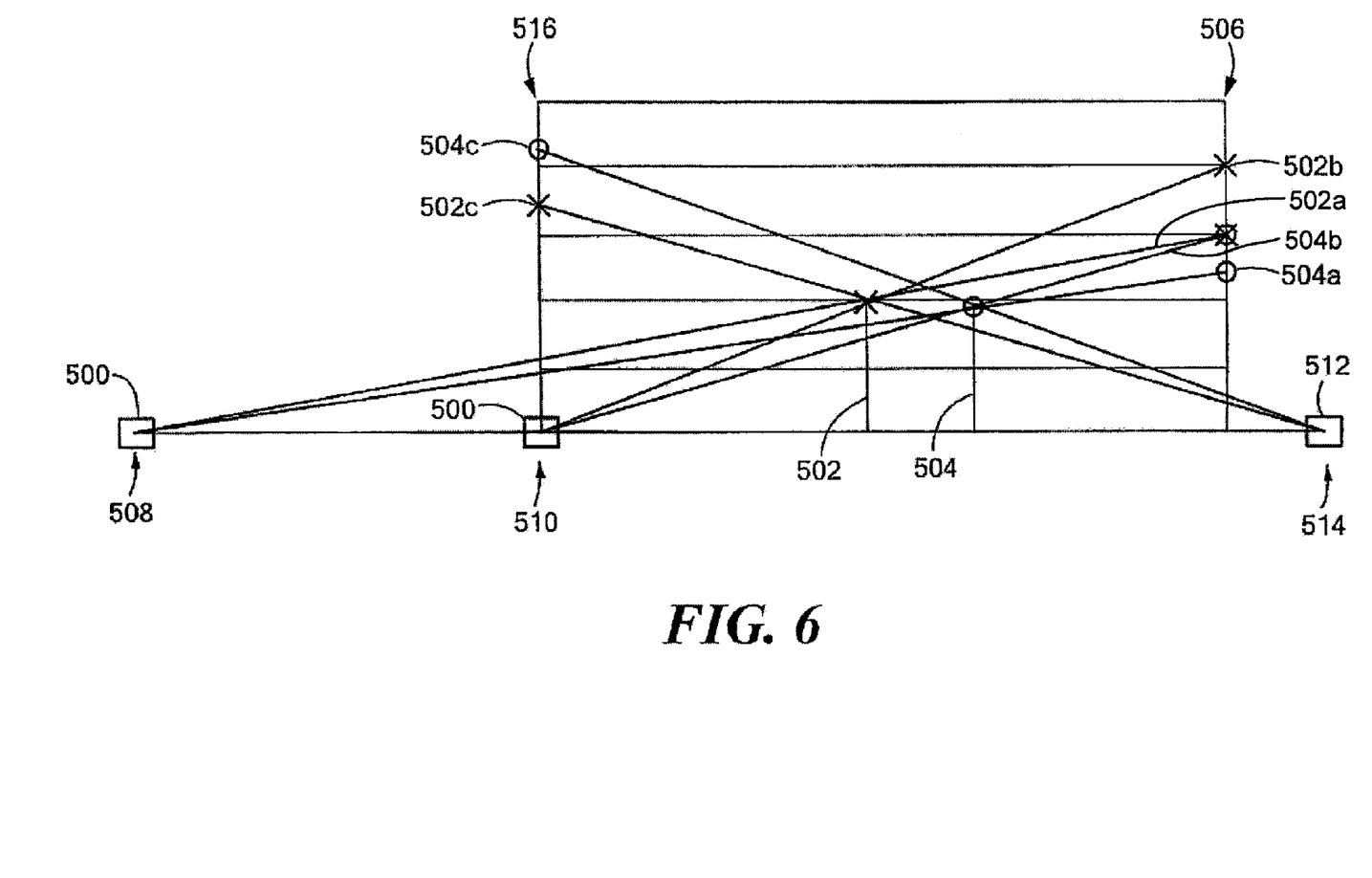
FIG. 6 is a schematic of an imaging system which generates images from different sides of an object.

Referring now to FIG. 6, the imaging techniques described above in conjunction with FIGS. 1-5 can be extended to utilize variable magnification of an object from two different directions about the object including directly opposite directions (i.e. opposing directions) about the object.

As described above, X-ray tomosynthesis can be achieved by using images in which the x-ray beam passes through tissues from different angles to create parallax shifts between the images for the structures being imaged. This can be accomplished using magnification images. In magnification x-ray imaging, a divergent beam passes through the tissues at differing angles depending upon the distance of the x-ray source from the structures in the objects being imaged. These images can then by synthesized into tomographic slices.

Another technique for using magnification x-ray imaging to permit tomosynthesis would be to obtain images from one side of an object and then obtaining images from the opposite side (or direction) of the object (i.e. the second side being 180 degrees from the first side). With this approach, structures in the same plane on both images can be closely registered and reinforced while structures in all other planes will be misregistered and blurred thus emphasizing the structures in the registered plane. The images can then be shifted so that the next plane is registered, etc to provide all planes through the structure.

For example in FIG. 6, structure 502 will be projected as 502c on the detector when the source is on one side and then it will be projected as 502b when the source is on the other side. When the two images are adjusted so that the projection of 502 is identical on both images and thus, reinforced, the projection of object 504 will be misregistered on both images and will not be as clearly seen as object 502. By adjusting the original two images, object 504 can be registered in both images and reinforced while object 502 will no longer be registered and will not be reinforced. This can be done for all planes.

In FIG. 6, a first source 500 images first and second objects 502, 504 onto a plane defined by a first detector 506. As described above, the distance between the source 500 and the objects 502, 504 (or the distance between the objects and the detector) is changed to achieve variable magnification projections of the objects 502, 504. That is to say, due to variable parallax generated by magnification imaging, the requisite number of views (or projections) required to synthesize tomosynthesis slices is provided. In this manner a plurality of projections can be generated (e.g. at least one projection at each of a plurality of different magnification levels) which can be synthesized into tomosynthesis slices. Thus, in the example shown in FIG. 6, the source 500 is moved from position 508 to position 510. By changing the distance between the source 500 and the object 502, two projections are provided. Specifically, projection 502a is provided with the source 500 at location 508 and projection 502b is provided with the source 500 at location 510.

Similarly, by changing the distance between the source 500 and the object 504 (i.e. by moving the source location from location 508 to location 510), two projections are provided. Specifically, projection 504a is provided with the source at location 508 and projection 504b is provided with the source at location 510.

The system includes a second source 512 disposed at a location 514. Source 512 images the first and second object 502, 504 onto a plane defined by a second detector 516. Thus, with the source disposed at location 514, projection 502c (i.e. a projection of object 502 generated using source 514 and detector 516) and projection 504c (i.e. a projection of object 502 generated using source 514 and detector 516) are provided.

It should be noted that the two sources 500 and 512 are disposed on different sides of the objects 502, 504 being imaged. Parallax shifts will differ for objects in each plane by image from opposite directions even with fixed source/detector and x-ray source to imaging object distance by imaging from opposite directions by using a divergent x-ray beam. For example, if an object is in the center of a structure, and it is imaged with a source that is equidistant from the object in the 180 degree projections, then the magnification of the object will be the same on both images and when they are registered they will superimpose and be reinforced while all other planes (due to differing magnification) will be misregistered and not reinforced. By changing the size of the images, the next plane will be reinforced while objects out of that plane will be misregistered, etc. In this manner tomosynthesis slices can be accomplished as well.

It should be appreciated that although source 500 is shown to be moved between two different locations (i.e. locations 508 and 510), while source 512 is shown in only one location, other variations of source movement can also be used. For example, source 512 can be moved to a plurality of locations while source 500 is held stationary. Alternatively, both source 500 and source 512 can be moved to different positions along a straight path to thus change the distance between each of the sources and the objects being images.

Alternatively still, and as described above, the detectors 506, 516 (rather than the sources 500, 512), can be moved to change the magnification at which objects being imaged are measured. Or the source-detector pair can be moved along a straight path in the direction toward or away from objects being imaged. Or alternatively still, both the sources and the detectors can be moved independently of each other. It should thus be appreciated that any combination of movement of sources and detectors which results in variable magnification projections of the objects can be used so long as the movements of the sources and/or detectors also results in projections (or more accurately, perhaps, projection data) which can be used to generate images that can be synthesized into tomosynthesis slices.

It should be understood that the dual imaging approach described in conjunction with FIG. 6, can be used in combination with the techniques and embodiments described in conjunction with FIGS. 1-5.

Although only a few exemplary embodiments of this invention have been described in detail above, those of ordinary skill in the art will readily appreciate that many modifications are possible in the exemplary embodiments without materially departing from the novel teachings and advantages of this invention. Accordingly, all such modifications are intended to be included within the scope of this invention as defined in the following claims. It should further be noted that any patents, applications and publications referred to herein are incorporated by reference in their entirety.

What is claimed is:

1. A method for producing a medical image of a subject, the method comprising the steps of:
   a) disposing the subject between a source emitting a divergent beam of x- rays and a detector having an imaging plane configured to receive x-rays emitted by the source;
   b) acquiring a series of projection images of the subject at a plurality of magnification levels by translating at least one of the source and detector along a central axis substantially normal to the imaging plane of the detector; and
   c) reconstructing a three-dimensional image of the subject from the series of projection images acquired at the plurality of magnification levels.

2. The method as recited in claim 1 wherein step b) further comprises rotating the source and detector along an arced path about the subject such that the series of projection images is acquired at the plurality of magnification levels and at a plurality of angles about the subject and step c) further comprises reconstructing the three dimensional image with reduced artifact levels from the series of projection images acquired at the plurality of magnification levels and the plurality of angles.

3. The method as recited in claim 1 wherein step b) further comprises acquiring a first series of projection images at the plurality of magnifications levels at a first angle and acquiring a second series of projection images at another plurality of magnifications levels at a second angle opposite the first angle and step c) includes reconstructing an image from the first and second series of projection images such that subject features in equivalent depth planes encoded in the first and second series of projection images are registered and reinforced, while structures in other depth planes are misregistered and blurred.

4. The method as recited in claim 3 wherein translating at least one of the source and detector changes an angle at which the x-ray beam passes through the subject and reaches the imaging plane of the detector.

5. The method as recited in claim 3 wherein step c) further comprises recovering depth information encoded in an apparent movement of the subject between projection images at different magnification levels.

6. The method as recited in claim 3 wherein step b) further comprises translating of at least one of the source and detector is performed at a pseudo-random pattern along the central axis.

7. The method as recited in claim 1 wherein subject radiation exposure is reduced by decreasing an intensity of the x-ray beam as the source is translated closer to the subject.

8. The method as recited in claim 1 wherein subject radiation exposure is reduced by employing a narrow x-ray beam to reduce irradiation of structures within the subject that are not being imaged.

9. A tomographic system for producing a medical image of a subject, the system comprising:
   an x-ray source configured to emit a divergent beam of x-rays that passes through the subject;
   a detector having an imaging plane configured to receive the x-rays emitted by the source;
   a controller configured to direct an acquisition of a series of projection images from the subject at a plurality of magnification levels by translating at least one of the source and detector along a central axis substantially normal to the imaging plane of the detector; and
   a processor configured to reconstruct a three-dimensional image of the subject from the series of projection images acquired at the plurality of magnification levels.

10. The tomographic system as recited in claim 9 wherein reconstructing the three-dimensional image of the subject includes recovering depth information encoded in an apparent movement of the subject between projection images at different magnification levels.

11. The tomographic system as recited in claim 9 further comprising a telescoping arm coupled at one end to the source and at an opposite end to the detector and wherein translating at least one of the source and detector along the central axis includes at least one of extending the telescoping arm and retracting the telescoping arm.

12. The tomographic system as recited in claim 11 wherein:
- the controller is further configured to direct a rotating of the telescoping arm about a pivot point such that the source and detector traverse an arced path about the subject and the series of projection images is acquired at the plurality of magnification levels and a plurality angles about the subject; and
- the processor is further configured to reconstruct the three-dimensional image of the subject with reduced artifacts from the series of projection images acquired at the plurality of magnification levels and the plurality of angles.

13. The tomographic system as recited in claim 9 wherein a first series of projection images is acquired at the plurality of magnification levels at a first angle and a second series of projection is acquired at another plurality of magnification levels at a second angle opposite the first angle and the processor is further configured to reconstruct an image of the subject from the first and second series of projection images such that subject features in equivalent depth planes encoded in the first and second series of projection images are registered and reinforced, while structures in remaining depth planes are misregistered and blurred.

14. The tomographic system as recited in claim 9 further comprising a pair of compression plates configured to hold the subject at a fixed location between the source and detector.

15. The tomographic system as recited in claim 14 wherein the fixed location is offset from a center of the imaging plane.

16. The tomographic system as recited in claim 9 further comprising a grid coupled to the imaging plane and configured to reject x-ray scatter.

17. The tomographic system as recited in claim 9 wherein subject radiation exposure is reduced by decreasing an intensity of the x-ray beam as the source is translated closer to the subject.

18. A tomographic system for producing a medical image of a subject, the system comprising:
- a first x-ray source disposed at a first side of the subject and configured to emit a divergent beam of x-rays that passes through the subject;
- a first detector disposed at a second side of the subject opposite the first side and having an imaging plane configured to receive the x-rays emitted by the first x-ray source;
- a second x-ray source disposed at the second side of the subject and configured to emit a divergent beam of x-rays that passes through the subject;
- a second detector disposed at the first side of the subject and having an imaging plane configured to receive the x-rays emitted by the second x-ray source;
- a controller configured to direct an acquisition of a first series of projection images from the subject at a first magnification level using the first source and detector and direct an acquisition of a second series of projection images from the subject at a second magnification level using the second source and detector, the second magnification level being different than the first magnification level; and
- a processor configured to reconstruct a medical image from the first and second series of projection images such that subject features in equivalent depth planes encoded in the first and second series projection of images are registered and reinforced, while structures in remaining depth planes are misregistered and blurred.

* * * * *

UNITED STATES PATENT AND TRADEMARK OFFICE
CERTIFICATE OF CORRECTION

PATENT NO. : 7,885,378 B2  Page 1 of 1
APPLICATION NO. : 12/090314
DATED : February 8, 2011
INVENTOR(S) : Daniel B. Kopans et al.

It is certified that error appears in the above-identified patent and that said Letters Patent is hereby corrected as shown below:

Column 3, line 28, "abreast" should be --a breast--.

Column 3, line 59, "images" should be --imaging--.

Claim 3, Column 12, line 15, "magnifications" should be --magnification--.

Claim 3, Column 12, line 17, "magnifications" should be --magnification--.

Signed and Sealed this
Twenty-second Day of March, 2011

David J. Kappos
*Director of the United States Patent and Trademark Office*